United States Patent [19]

Swim et al.

[11] Plant 5,168

[45] Jan. 3, 1984

[54] ROSE PLANT CV. AROCAD

[75] Inventors: Herbert C. Swim; Jack E. Christensen, both of Ontario, Calif.

[73] Assignee: Armstrong Nurseries, Inc., Ontario, Calif.

[21] Appl. No.: 390,924

[22] Filed: Jun. 22, 1982

[51] Int. Cl.[3] ..... A01H 5/00

[52] U.S. Cl. ..... Plt./16

[58] Field of Search ..... Plt./16-17

*Primary Examiner*—Robert E. Bagwill

*Attorney, Agent, or Firm*—Synnestvedt & Lechner

[57] ABSTRACT

A hybrid tea having blossoms of a rich apricot color, produced on strong stems.

1 Drawing Figure

This invention relates to a new class of hybrid tea rose cv. "Arocad". The plant is a half-hardy outdoor seedling of the bush type, cultivated for garden decoration. It was propagated by Herbert C. Swim and Jack E. Christensen in Ontario, Calif., having as its seed parent "First Prize", U.S. Plant Pat. No. 2,774, and, as its pollen parent "Golden Wave", U.S. Plant Pat. No. 2,105, by budding on Dr. Huey understock. It holds its distinguishing characteristics through succeeding propagations by budding.

The new variety Arocad is characterized by its rich apricot flower coloration that is deeper than any other apricot rose known as of this date. The plant is above average in plant vigor (significantly more vigorous and productive than either parent) which results in many more flowers and a bushier, more full plant than other rose cultivars in the apricot tones. An abundance of large, well-formed flowers are produced by Arocad rose plants on strong stems of suitable lengths for cutting. The cultivar shows above-average disease resistance under Ontario, Calif. conditions and this is unusual for apricot-colored rose cultivars.

This new cultivar may be distinguished from its seed parent, First Prize, by the following characteristics:

First Prize bears flowers blended with several shades of pink, whereas the new rose Arocad bears flowers of a relatively uniform apricot coloration essentially as described and illustrated herein. The Arocad rose produces an upright bush of medium height, about 4 to 5 feet, whereas First Prize produces a significantly shorter bush of medium height with an upright-spreading habit.

The new rose Arocad is a vigorous bush of above-average disease resistance in the Ontario, Calif. area, whereas the seed parent, First Prize, is a bush of significantly less vigor and exhibits a significantly lower level of disease resistance under conditions prevailing in the Ontario, Calif. area.

This new cultivar may be distinguished from its pollen parent, Golden Wave, by the following characteristics:

Golden Wave normally bears flowers of a relatively uniform deep yellow coloration, whereas the new cultivar Arocad bears flowers of an apricot coloration essentially as described and illustrated.

The pollen parent, Golden Wave, as bred and commercialized primarily for use in the production of greenhouse grown cut roses, whereas the new rose Arocad is only suitable for garden decoration.

The flowers of the new rose have only a slight tea fragrance, whereas the flowers of Golden Wave have a significantly stronger fruity fragrance.

The new rose cultivar is very vigorous whereas Golden Wave is a bush of significantly less vigor.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon The R.H.S. Colour Chart published by The Royal Horticultural Society of London, England.

FLOWER

The flowers of the cultivar as grown in Ontario, Calif. are usually borne singly (but sometimes two or more to a stem in an irregular rounded cluster) on strong medium to long length stems. The plants provide abundant quantity of blooms when grown outdoors and bloom nearly continuously during the growing season. The flowers have a slight tea fragrance.

BUD

The peduncle is average length to long, and average caliper, erect and stiff. It is almost smooth with some stipitate glands. The color ranges from Yellow-Green, 144 to Yellow Green, 146A.

Before the calyx breaks, the bud is medium to large in size, and medium-length to long, pointed and ovoid in form, with some stipitate glands on the surface of the bud. There are usually slender foliaceous parts extending beyond the tip of the bud equal to one-fourth to one-half of its length.

As the calyx breaks, the color is near Orange, 26A.

The inner surface of the sepals has a fine, wooly tomentum; margins are lined with stipitate glands and hairs.

As the first petal opens, the bud is large in size, medium-length to long and pointed and ovoid in form. The color on the outside of the petal is between Orange, 26A and Orange-Red, 33B. The inside surface of the petal is between Orange, 26A and Orange, 24A with the basal attachment zone near Yellow-Orange, 15B. The bud opens up well and is not prevented from opening by hot, wet or dry weather.

BLOOM

The size of the bloom when fully open is average to large, ranging from 4 to 5 inches. The petalage is double, with from 25 to 30 petals, plus from 0 to 5 petaloids, arranged regularly. The bloom is full and high centered at first, becoming open and high centered. At first, the petals remain somewhat cupped, with tips reflexed outward, becoming, later at maturity, loosely cupped with tips reflexed outward.

The petals are of medium thickness with the inside velvety and the outside satiny. The outside petals are broadly obovate with flat apex. The intermediate petals are round to broadly obovate with flat apex. The inside petals are obovate with rounded apex. The colors may be modified by being shaded and/or washed or tinted with other colors.

The paragraphs immediately following describe the color values observed in a flower newly opened in the month of May. The plant had been grown outdoors in Ontario, Calif.

The outer surface of the outside petal was between Orange-Red, 32D and Orange, 29C. The inner surface of the outside petal was between Orange-Red, 33C and Orange, 26B with basal attachment zone of near Yellow-Orange, 15B.

The outer surfaces of both the intermediate petals and the outside petals were between Orange-Red, 33C and Orange, 26B. The inner surfaces of both the intermediate and the inner petals were between Orange, 24B and Yellow-Orange, 22B with a small basal attachment zone of near Yellow-Orange, The paragraph immediately following describes color values observed in a bloom which had been open for three days, in the outdoors, in the month of May. The plant had been grown outdoors in Ontario, Calif.

The outer surface of petals were between Red, 37C and Red, 36A. The inner surface of outside petals showed a basal attachment zone of near Yellow-Orange, 15D that suffuses to between Orange, 29D and 27B.

The outside surfaces of the inside petals were between Red, 36A and Orange-Red, 35D. The inside surface of the inside petals shows a basal attachment zone near Yellow-Orange, 15C that suffuses to between Orange, 24D and 29D.

The general color effect of the newly opened flower is between Orange, 24C and 25C. The bloom after being three days open gives a general color effect which is between Orange, 29D and 24D. The petals drop off cleanly and are not particularly affected by cold, hot, wet or dry weather.

In May, flowers on the bush in the garden persist for 4 to 5 days outdoors and kept at living-room temperatures will last from 4 to 6 days in the month of May.

REPRODUCTIVE ORGANS

The stamens are many in number, arranged regularly about the pistils.

The filaments are from short to medium-length.

The anthers are medium size to large, all opening approximately at once, the coloration when immature being near Yellow-Orange, 21C; the mature anthers being near Brown, 200B.

Pollen is abundant and near Yellow-Orange, 21D in color.

There are many pistils, being approximately 110 in number.

The styles are very uneven, from short to average length, heavy caliper and somewhat bunched. The color is near Red, 46B.

The stigma is near Yellow, 4B in color.

The ovaries are of average length and are enclosed in the calyx.

The hips are of average length, globular in shape and near Yellow-Green, 153A in color. They are moderately smooth and have thick, fleshy walls.

The sepals are permanent, medium to long in length, and spear-shaped. The color on the inside is near Yellow-Green, 145C, and near Yellow-Green, 144C on the outside.

Seeds vary from average to many (usually from 15 to 25 in number) and are of medium to large in size.

FOLIAGE

The compound leaves usually comprise from three to five leaflets. There is an abundant amount of such leaves, which are of medium to large in size, moderately heavy to somewhat leathery and semi-glossy. The leaflets are ovoid in shape with an acute apex, and with a round to acute base and with doubly serrated margins.

The mature foliage displays upon its upper surface a color which is between Yellow-Green, 147A and Green, 139A. The under surface is near Yellow-Green, 148B.

The young foliage on its upper surface is near Greyed-Purple, 187A in color. On its under surface, it is near Greyed-Purple, 184B in color.

The rachis is average size to heavy, grooved, glandular, with some stipitate glands on the edges; the under side being sparsely prickly and having stipitate glands.

The stipules are medium to long in length, narrow to medium in width, with medium length points, turning out at an angle of less than 45° and recurving toward the stem.

The plant displays a more than average resistance to mildew and blackspot compared to other commercial varieties grown in the locality named under comparable conditions.

GROWTH

The plant is of upright-bushy habit, and considerably branched. It displays a very vigorous growth. The canes are of medium to heavy caliper.

The main stems are near Yellow-Green, 146D in color. They bear several large prickles of medium-length and which are almost straight and with a medium-length, moderately broad base. The color is near Greyed-Orange 177C. There are few small prickles near Greyed-Orange, 177C in color and no hairs.

The branches are a color between Yellow-Green, 146B and 147A. They bear several to many large prickles, which are of a medium-length, almost straight and with a medium-length, moderately broad base. The color is near Yellow-Green, 144B and blushed lightly with near Greyed-Purple, 183C. There are several small prickles and several hairs both having the same coloration as the large prickles.

New shoots are near Greyed-Purple, 184B in color. They bear several to many large prickles, which are of a medium length, almost straight and with medium-length, moderately broad base. The color is near Yellow-Green, 144B. There are several to many small prickles and many hairs, both having the coloration of the large prickles.

We claim:

1. A new and distinct variety of rose plant of the hybrid tea class, substantially as herein shown and described, being particularly characterized in its rich apricot flower coloration, its plant vigor, and the abundance of large, well-formed flowers produced on strong stems of a length suitable for cutting.

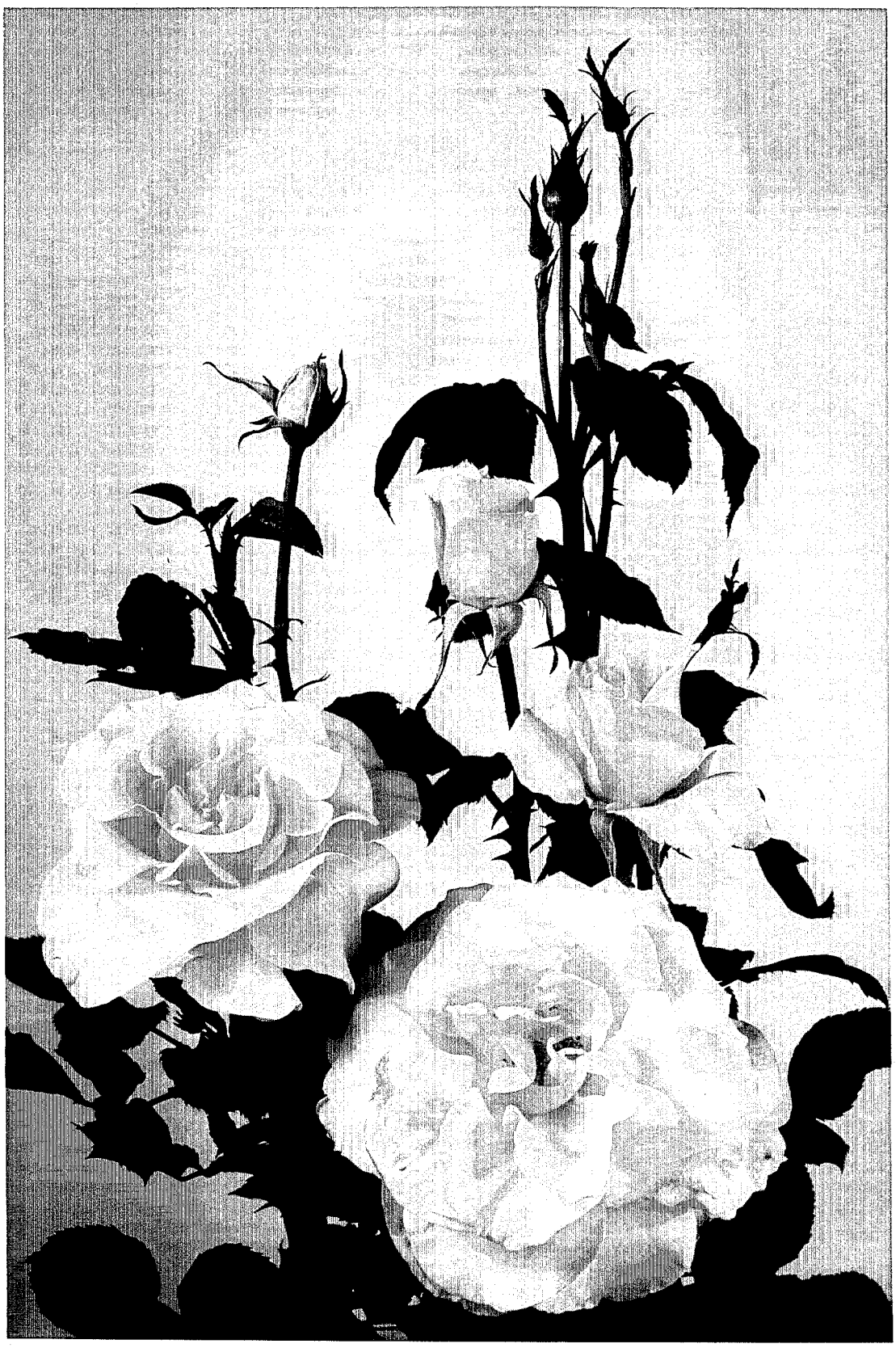

* * * * *